United States Patent [19]

Cliffe

[11] Patent Number: 5,710,149
[45] Date of Patent: Jan. 20, 1998

[54] PIPERAZINE DERIVATIVES AS 5-HT ANTAGONISTS

[75] Inventor: Ian Anthony Cliffe, Slough, England

[73] Assignee: John Wyeth & Brother, Ltd., Maidenhead, England

[21] Appl. No.: 731,953

[22] Filed: Oct. 23, 1996

Related U.S. Application Data

[63] Continuation of Ser. No. 244,604, filed as PCT/GB92/02228, Dec. 1, 1992, abandoned.

[30] Foreign Application Priority Data

Dec. 5, 1991 [GB] United Kingdom ............ 9125900

[51] Int. Cl.$^6$ ............ A61K 31/55; A61K 31/495; C07D 405/14; C07D 405/10
[52] U.S. Cl. ............ 514/212; 514/230.5; 514/235.8; 514/254; 540/481; 540/598; 544/105; 544/121; 544/357; 544/364; 544/372; 544/376; 544/377
[58] Field of Search ............ 540/481, 598; 544/357, 105, 364, 372, 376, 377, 121; 514/212, 254, 230.5, 235.8

[56] References Cited

U.S. PATENT DOCUMENTS

| | | | |
|---|---|---|---|
| 4,788,290 | 11/1988 | Stack | 544/377 |
| 4,935,511 | 6/1990 | Youssefyeh et al. | 544/105 |
| 4,988,814 | 1/1991 | Abou-Gharbia et al. | 544/295 |
| 5,340,812 | 8/1994 | Cliffe | 514/255 |
| 5,369,103 | 11/1994 | Cliffe et al. | 514/211 |
| 5,382,583 | 1/1995 | Cliffe | 514/252 |
| 5,430,033 | 7/1995 | Cliffe et al. | 514/254 |

FOREIGN PATENT DOCUMENTS

| | | |
|---|---|---|
| 0138280 | 4/1985 | European Pat. Off. |
| 0481744 | 4/1992 | European Pat. Off. |
| 2230781 | 10/1990 | United Kingdom |

*Primary Examiner*—Emily Bernhardt
*Attorney, Agent, or Firm*—Arthur G. Seifert

[57] ABSTRACT

This invention concerns compounds of formula (I)

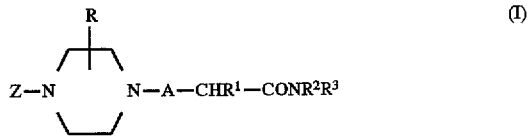

where A is a $C_1$ or $C_2$ alkylene chain optionally substituted by lower alkyl; Z is a bicyclic oxygen-containing aryl radical (e.g. 2,3-dihydro-1,4-benzodioxin-5-yl); R is hydrogen or lower alkyl; $R^1$ is aryl or aryl(lower)alkyl; $R^2$ is hydrogen or lower alkyl; and $R^3$ is hydrogen, an alkyl group of 1 to 10 carbon atoms, cycloalkyl of 3 to 12 carbon atoms; cycloalkyl(lower)alkyl, aryl or aryl(lower)alkyl or $R^2$ and $R^3$ together with the nitrogen atom to which they are both attached represent a saturated heterocyclic ring which may contain a further hetero atom, and the pharmaceutically acceptable acid addition salts thereof. The compounds are 5-HT$_{1A}$-antagonists which may be used, for example, in treating anxiety.

7 Claims, No Drawings

PIPERAZINE DERIVATIVES AS 5-HT ANTAGONISTS

This application is a continuation of application Ser. No. 08/244,604 filed as PCT/GB92/02228, Dec. 1, 1992, now abandoned.

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

GB 2230781-A and GB 2230780-A disclose related piperazine derivatives which exhibit 5-HT$_{1A}$ receptor affinity.

The novel compounds of the invention are those of the general formula

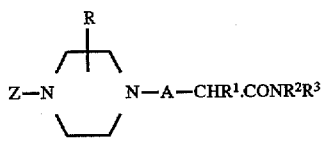

(I)

and the pharmaceutically acceptable acid addition salts thereof.

In formula (I)

A is an alkylene chain of 1 or 2 carbon atoms optionally substituted by one or more lower alkyl groups, Z is a bicyclic oxygen-containing radical of the formula

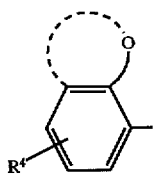

wherein the heterocyclic ring containing the oxygen atom contains a total of 5 to 7 ring members, said heterocyclic ring being saturated or unsaturated, being optionally substituted (e.g. by one or more substituents R$^5$ where R$^5$ has the meaning given for R$^4$ below) and optionally containing one or more hetero ring members (e.g. —O—, —NR$^2$— where R$^2$ is hydrogen or lower alkyl, —S— or —SO$_2$—) in addition to the oxygen atom illustrated, R represented hydrogen or one or two same or different lower alkyl groups R$^1$ is an aryl radical or an aryl(lower)alkyl radical R$^2$ is hydrogen or lower alkyl R$^3$ is hydrogen, an alkyl group of 1 to 10 carbon atoms, cycloalkyl of 3 to 12 carbon atoms, cycloalkyl(lower)alkyl, aryl or aryl(lower)alkyl or R$^2$ and R$^3$ together with the nitrogen atoms to which they are both attached represent a saturated heterocyclic ring which may contain a further hetero atom (e.g. an azetidino, pyrrolidino, piperidino, hexahydroazepino, heptamethyleneimine, morpholino or piperazino ring which may be optionally substituted by lower alkyl, aryl or aryl (lower)alkyl)

R$^4$ represents hydrogen or one or more same or different substituents selected from lower alkyl, halogen, halo(lower)alkyl (e.g. trifluoromethyl), nitro, nitrile, oxo, hydroxy, (lower)alkoxy, hydroxy(lower)alkyl, (lower)alkoxy(lower alkyl), lower alkanoyloxy(lower alkyl), (lower) alkylcarbonyl, (lower)alkylcarbonyl—(lower)alkyl, carbamoyl amino, acylamino (e.g. loweralkanoylamino), (lower)alkylamino or di(lower)alkylamino.

The term "lower" as used herein means that the radical referred to contains 1 to 6 carbon atoms. Preferably such radicals contain 1 to 4 carbon atoms. Examples of alkyl radicals are methyl, ethyl, propyl, isopropyl, butyl, isobutyl, sec-butyl, tert-butyl, pentyl and isopentyl. When R$^3$ is an alkyl radical a particularly preferred radical is a tertiary alkyl radical such as tert-butyl. Examples of cycloalkyl groups of 3 to 12 carbon atoms include cyclopropyl, cyclobutyl, cyclopentyl, cyclohexyl and cycloheptyl. Cycloalkyl groups also include bicyclic, tricyclic and tetracyclic groups e.g. adamantyl.

Preferred examples of the group Z are those of the formulae

(a)

(b)

(c)

(d)

(e)

-continued

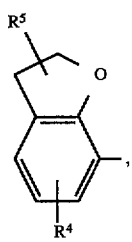
(f)

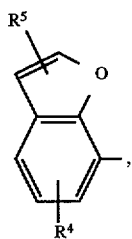
(g)

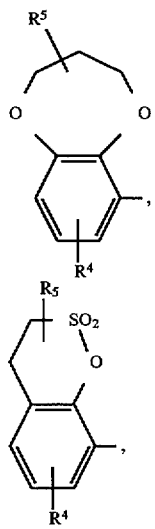
(h)

(i)

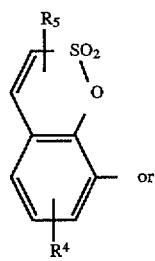
(j)

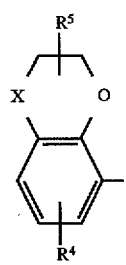
or (k)

where $R^4$ is as defined above, $R^5$ has the definition of $R^4$ given above and X is —S—, —NR$^6$— where $R^6$ is hydrogen or lower alkyl or —CO—.

When used herein "aryl" means an aromatic radical having 6 to 12 carbon atoms (e.g. phenyl or naphthyl) which optionally may be substituted by one or more substituents commonly used in medicinal chemistry, e.g. substituents such as lower alkyl, lower alkoxy, lower alkylthio, halogen, trifluoromethyl, nitro, carbalkoxy, carbamoyl, cyano, amino, (lower)alkylamino and di(lower)alkylamino.

Examples of aryl(lower)alkyl include, for example, benzyl in which the phenyl group may be substituted as defined above.

Examples of preferred compounds are (A) those in which A is ethylene
(B) those in which $R^2$ is hydrogen and $R^3$ is tert-alkyl or cycloalkyl
(C) those in which NR$^2$R$^3$ represents a piperidino or hexahydroazepino ring
(D) those in which Z has the formula (a) especially those in which $R^4$ and $R^5$ are both hydrogen or one is hydrogen and the other is hydroxymethyl
(E) those in which R is hydrogen
(F) those in which $R^1$ is phenyl The compounds of the invention may be prepared by methods known in the art from known starting or starting materials that may be prepared by conventional methods. One method comprises alkylation of a piperazine compound of formula

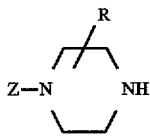
(II)

(where Z and R are as defined above) with an alkylating agent providing the group

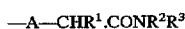
(III)

(where A, $R^1$, $R^2$ and $R^3$ have the meanings given above)

The alkylating agent may be, for example a compound of formula

(IV)

where A, $R^1$, $R^2$ and $R^3$ are as defined above and X is a leaving group such as halogen or an alkyl- or arylsulphonyloxy group. Alternatively the alkylating agent may be an unsaturated compound of formula

(V)

(where $R^1$, $R^2$ and $R^3$ are as defined above) and the compound of formula (V) is reacted with the piperazine of formula (II) by means of a Michael reaction.

The starting piperazine of formula II may be prepared, for example, by the methods disclosed in EP-A-138280 and EP-A-372657.

In an alternative method of preparing the compounds of the invention an amine of formula

(VI)

(where $R^2$ and $R^3$ are as defined above) is acylated with an acid of formula

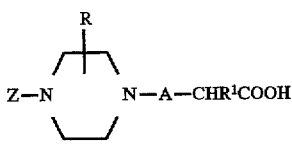

(VII)

(where Z, A, R and $R^1$ are as defined above) or with an acylating derivative thereof. Examples of acylating derivatives include the acid halides (e.g. acid chlorides), azides, anhydrides, imidazolides (e.g. obtained from carbonyldiimidazole), activated esters or O-acyl ureas obtained from a carbodiimide such as a dialkylcarbodiimide particularly dicyclohexylcarbodiide. Preferably the amine is acylated with the acid in presence of a coupling agent such as 1,1'-carbonyldiimidazole, iso-butylchloroformate or diphenylphosphinyl chloride.

The acids of formula (VII) may be prepared by methods known in the art e.g. from the piperazine derivatives of formula (II). For example a piperazine derivatives of formula (II) may be reacted with an acid of formula

$CH_2{=}CHR^1COOH$ by means of a Michael Reaction.

A further method of preparing the compounds of the invention comprises reacting a compound of formula (VIII)

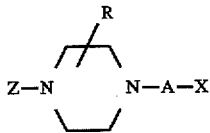

(VIII)

where Z, A and R are as defined above and X is a leaving group, such as halogen (e.g. chlorine), with an anion of an amide of formula

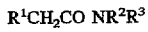

$R^1CH_2CO\ NR^2R^3$ (IX)

(where $R^1$, $R^2$ and $R^3$ are as defined above and where preferably $R^2$ is other than hydrogen). The anion may be prepared by reacting the amide with a strong base e.g. butyl lithium, potassium hydride or lithium diisopropylamide.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain one or more asymmetric carbon atoms, so that the compounds can exist in different steroisomeric forms. All steroisomeric forms are included within the invention. The compounds can be, for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors, particularly receptors of the $5\text{-HT}_{1A}$ type. In general, the compounds selectively bind to receptors of the $5\text{-HT}_{1A}$ type to a much greater extent than they bind to other receptors such as $\alpha_1$. The compounds possess $5\text{-HT}_{1A}$ antagonistic activity. The compounds can be used for the treatment of CNS disorders, such as anxiety in mammals, particularly humans. They may also be useful as antidepressants, hypotensives and as agents for regulating the sleep-wake cycle, feeding behaviour and/or sexual function and for treating cognition disorders.

The compounds of the invention are tested for $5\text{-HT}_{1A}$ receptor binding activity in rat hippocampal membrane homogenated by the method of B. S. Alexander and M. D. Wood, J Pharm Pharmacol, 1988, 40, 888–891. The compound of Example 8, which is a representative compound of the invention, had an $IC_{50}$ of 0.6 nM in this test procedure.

The compounds are tested for $5\text{-HT}_{1A}$ receptor antagonism activity in a test involving the antagonism of 5-carboxamido-tryptamine in the guinea-pig ileum in vitro (based upon the procedure of Fozard et al, Br. J. Pharmac., 1985, 86, 601P). The compound of Example 8 had a $pA_2$ of 9.4 in this test procedure.

The invention also provides a pharmaceutical composition comprising a compound of formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided olid which is in admixture with the finely divided active ingredient. In tablets the active ingredient is mixed with a carrier having the necessary compression properties in suitable proportions and compacted in the shape and size desired. The powders and tablets preferably contain up to 99% e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention.

EXAMPLE 1

5-Nitro-2,3-dihydro-1,4-benzodioxin 1,2-Dibromoethane (12.0 g, 0.064 mol), potassium carbonate (17.6 g, 0.127 mol) and tetra-n-butyl ammonium bromide (1.37 g, 0.0043 mol) were added to a stirred solution of 3-nitrocatechol (6.59 g, 0.043 mol) in toluene (210 ml). The solution was heated at reflux with azeotropic removal of water for 23 h, cooled to room temperature, washed with 2N sodium hydroxide solution (150 ml), dried ($Na_2SO_4$) and evaporated in vacuo to give an orange oil. Purification by column chromatography (silica; ether) gave the product (2.55 g) m.p. 55°–59° C.

EXAMPLE 2

2,3-Dihydro-1,4-benzodioxin-5-amine

Ammonium formate (3.40 g, 0.054 mol) and 10% passadium on charcoal (1.44 g) were added to a stirred solution of the product of Example 1 (2.45 g, 0.0135 mol) in methanol (15 ml). After the considerable effervescence had ceased, the mixture was filtered, evaporated in vacuo and triturated with acetonitrile. The residue was purified by chromatography (silica; ether) to give the product (1.51 g).

EXAMPLE 3

1-(2,3-Dihydro-1,4-benzodioxin-5-yl)piperazine

A solution of the product of Example 2 (1.50 g, 0.010 mol) and bis(2-chloroethyl)amine hydrochloride (1.77 g 0.01 mol) in chlorobenzene (20 ml) was heated under reflux for 24 h, cooled to room temperature and evaporated in vacuo. The white solid was dissolved in aqueous sodium hydroxide (100 ml) and extracted into ethyl acetate (3×50 ml). The extracts were dried ($MgSO_4$) and evaporated in vacuo to give the product (2.00 g).

EXAMPLE 4

1-(2-Chloroethyl)-4-[5-(2,3-dihydro-1,4-benzodioxinyl]piperazine

A solution of the product from Example 3 (0.1 mol), 2-bromochloroethane (0.1 mol), and di-isopropylethylamine (0.1 mol) in dimethylformamide (250 ml) is stirred for 24 h and poured into water (500 ml). The mixture is basified with sodium hydroxide, extracted with ethyl acetate (3×250 ml) and the extracts washed with water (2×500 ml), dried ($MgSO_4$), and evaporated in vacuo. The residue is purified by chromatography (silica; ethyl acetate) to give the product.

EXAMPLE 5

2,3,4,5,6,7-Hexahydro-1-{4-[1-[4-(2,3-dihydro-1,4-benzodioxin-5-yl)piperazinyl]]-2phenylbutyryl}-1H-azepine Butyl lithium (1.5M in hexane; 5 ml) is added dropwise over 5 min, maintaining the temperature below 8° C., to a stirred solution of 2,3,4,5,6,7-hexahydro-1-phenylacetyl-1H-azepine (1.48 g, 6.8 mmol) and diisopropylamine (2.0 ml, 14 mmol) in dry toluene (16 ml) under argon. The mixture is stirred at 0° C. for 1 h and a solution of the product of Example 4 (6.8 mmol) in dry toluene (4 ml) is added dropwise. The mixture is stirred at 0° C. to 20° C. for 18 h, and water (50 ml) is added. The layers are separated, and the aqueous phase is extracted with ethyl acetate (2×50 ml). The combined organic phases are concentrated in vacuo. The crude product is purified by chromatography (silica; ethyl acetate) to give the title compound as the free base.

EXAMPLE 6

1-(2-Hydroxyethyl)-4-[5-(2,3-dihydro-1,4-benzodioxinyl]piperazine

A solution of the product from Example 3 (6.61 g, 0.03 mol), 2-bromoethanol (3.75 g, 0.03 mol), and triethylamine (3.53 g, 0.035 mol) in dimethylformamide (20 ml) was stirred for 18 h and poured into water (300 ml). The mixture was basified with sodium hydroxide, extracted with dichloromethane (3×100 ml) and the extracts washed with water (2×500 ml), dried ($MgSO_4$), and evaporated in vacuo to give an oil. A solution of the oil in ethyl acetate was acidified with ethereal hydrogen chloride. The precipitate was filtered and triturated with acetonitrile to give the hydrochloride salt of the product (4.03 g) as a white solid.

EXAMPLE 7

1-(2-Chloroethyl)-4-[5-(2,3-dihydro-1,4-benzodioxinyl]piperazine

A solution of the product of Example 6 (4.03 g, 0.012 mol) in chloroform (100 ml) was treated dropwise with thionyl chloride (6.52 g, 0.55 mol), stirred for 60 h, evaporated in vacuo, and the residue dissolved in water (200 ml). The solution was basified with sodium hydroxide, extracted with dichloromethane (3×100 ml), and the extracts dried ($MgSO_4$) and evaporated in vacuo to give the product (2.70 g) as a brown oil.

EXAMPLE 8

2,3,4,5,6,7-Hexahydro-1-{4-[1-[4-(2,3-dihydro-1,4-benzodioxin-5-yl)piperazinyl]]-2-phenylbutyryl}-1H-azepine A stirred suspension of potassium hydride (1.68 g, 0.042 mol) in anhydrous dimethylformamide (DMF, 20 ml) was treated dropwise with a solution of 2,3,4,5,6,7-hexahydro-1-phenylacetyl-1H-azepine (2.17 g, 0.01 mmol) in DMF (10 ml) under argon. The mixture was stirred for 1 h and a solution of the product of Example 7 (2.7 g, 0.0096 mmol) in DMF (10 ml) was added dropwise. The mixture was stirred for 18 h, treated dropwise with water (10 ml), and evaporated in vacuo. The residue was taken up into 0.1N-NaOH (200 ml) and extracted with ethyl acetate (3×100 ml). The extracts were dried (MgSO$_4$) and evaporated in vacuo to give an oil which was purified by chromatography (alumina; di-isopropylether). The product was isolated as the hydrochloride salt by precipitation of a white, non-crystalline solid with etheral hydrogen chloride (0.39 g), m.p. 102°–108° C. (Found: C, 63.7; H, 7.8; N, 7.7. $C_{28}H_{37}N_3O_3 \cdot HCl \cdot 1½ H_2O$ requires C, 63.8; H, 7.8; N, 8.0%).

I claim:
1. A compound of the formula

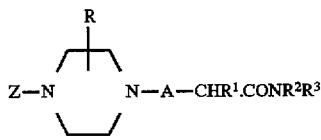
(I)

or a pharmaceutically acceptable acid addition salt thereof wherein

A is an alkylene chain of 1 or 2 carbon atoms optionally substituted by one or more lower alkyl groups, Z is a bicyclic oxygen-containing aryl radical of the formula

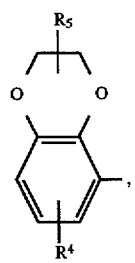
(a)

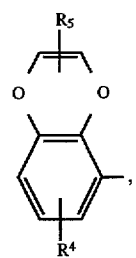
(b)

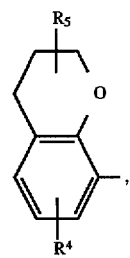
(c)

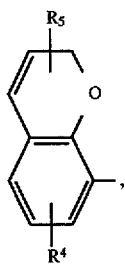
(d)

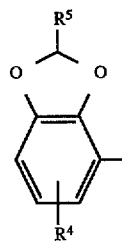
(e)

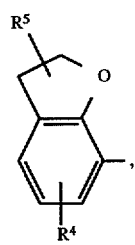
(f)

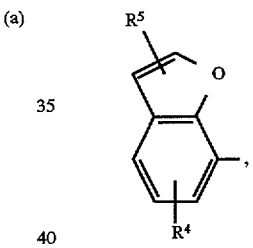
(g)

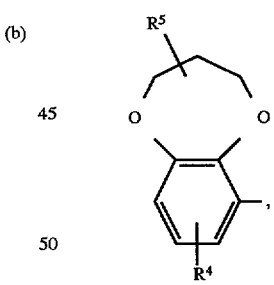
(h)

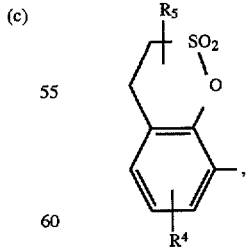
(i)

-continued

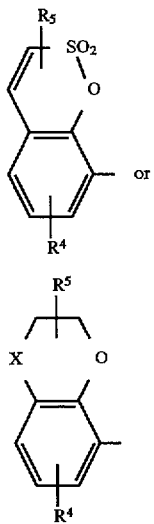

wherein $R^4$ and $R^5$ are, independently, hydrogen or one or more substituents selected from lower alkyl, hydrogen, halo(lower)alkyl, nitro, nitrile, oxo, hydroxy, (lower)alkoxy, hydroxy(lower)alkyl, (lower)alkoxy(lower alkyl), lower alkanoyloxy(lower alkyl), (lower)alkylcarbonyl, (lower) alkylcarbonyl(lower)alkyl, carboxamido, amino, loweralkanoylamino, (lower)alkylamino or di(lower) alkylamino and X is —S—, —NR$^2$, where $R^2$ is hydrogen, lower alkyl or —CO—;

R is hydrogen or one or two same or different lower alkyl groups;

$R^1$ is an aryl radical or an aryl(lower)alkyl radical;

$R^2$ is hydrogen or lower alkyl; and $R^3$ is hydrogen, an alkyl group of 1 to 10 carbon atoms, cycloalkyl of 3 to 12 carbon atoms, cycloalkyl(lower) alkyl, aryl or aryl(lower)alkyl or $R^2$ and $R^3$ together with the nitrogen atom to which they are both attached represent an azetidino, pyrrolidino, piperidino, hexahydroazepino, heptamethyleneimine, morpholino or piperazino ring which may be optionally substituted by lower alkyl, aryl or aryl(lower)alkyl, in which aryl is phenyl or naphthyl optionally substituted by one or more substituents selected from lower alkyl, lower alkoxy, loweralkylthio, halogen, trifluoromethyl, nitro, carbalkoxy, carboxamido, cyano, amino, (lower)alkylamino and di(lower)alkylamino.

2. A compound as claimed in claim 1 in which A is ethylene.

3. A compound as claimed in claim 1 in which $R^2$ is hydrogen and $R^3$ is tert-alkyl or cycloalkyl or in which —NR$^2$R$^3$ is a piperidino or hexahydroazepino ring.

4. A compound as claimed in claim 1 in which Z has the formula (a) defined in claim 2 and $R^4$ and $R^5$ are both hydrogen or one is hydrogen and the other is hydroxymethyl.

5. A compound as claimed in claim 1 which is 2,3,4,5,6, 7-hexahydro-1-{4-[1-[4-(2,3-dihydro-1,4-benzodioxin-5-yl)piperazinyl]]-2-phenylbutyryl}-1H-azepine or a pharmaceutically acceptable acid addition salt thereof.

6. A pharmaceutical composition comprising a compound claimed in claim 1 in association with a pharmaceutically acceptable carrier.

7. A method of treating a mammal suffering from anxiety or depression, comprising administering to such mammal an effective amount of a compound of formula I of claim 1 or a pharmaceutically acceptable salt thereof to alleviate such anxiety or depression.

* * * * *